United States Patent
Harks et al.

(10) Patent No.: US 8,774,906 B2
(45) Date of Patent: Jul. 8, 2014

(54) APPARATUS, METHOD AND COMPUTER PROGRAM FOR DETERMINING A PROPERTY OF A HEART

(75) Inventors: Godefridus Antonius Harks, Eindhoven (NL); Szabolcs Deladi, Eindhoven (NL); Bart Michiel De Boer, Eindhoven (NL); Maya Ella Barley, Eindhoven (NL); Jan Frederik Suijver, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 63 days.

(21) Appl. No.: 13/319,849

(22) PCT Filed: May 10, 2010

(86) PCT No.: PCT/IB2010/052040
§ 371 (c)(1),
(2), (4) Date: Jan. 17, 2012

(87) PCT Pub. No.: WO2010/131178
PCT Pub. Date: Nov. 18, 2010

(65) Prior Publication Data
US 2012/0116237 A1 May 10, 2012

(30) Foreign Application Priority Data
May 15, 2009 (EP) .................................. 09160428

(51) Int. Cl.
*A61B 5/0452* (2006.01)
(52) U.S. Cl.
USPC .......................................................... 600/509

(58) Field of Classification Search
None
See application file for complete search history.

(56) References Cited

U.S. PATENT DOCUMENTS

| 5,289,820 | A | 3/1994 | Beach et al. | |
|---|---|---|---|---|
| 6,600,948 | B2* | 7/2003 | Ben-Haim et al. | 600/512 |
| 2003/0171668 | A1 | 9/2003 | Tsujino et al. | |
| 2004/0039293 | A1* | 2/2004 | Porath et al. | 600/509 |
| 2004/0181139 | A1 | 9/2004 | Falwell et al. | |
| 2005/0283195 | A1 | 12/2005 | Pastore et al. | |

FOREIGN PATENT DOCUMENTS

| JP | 2008142568 | 6/2008 |
|---|---|---|
| WO | 9724981 A2 | 7/1997 |

* cited by examiner

*Primary Examiner* — Carl H Layno
*Assistant Examiner* — Paula J Stice (57) ABSTRACT

The present invention relates to an apparatus for determining a property of a heart. The apparatus comprises a catheter (5), which comprises a first property sensing unit for sensing a contraction signal indicative of a reoccurring local contraction of the heart (2) at a sensing site of the heart (2). The apparatus further comprises a first property determining unit (8) for determining the reoccurring local contraction of the heart (2) at the sensing site from the sensed contraction signal as a first property of the heart (2). The reoccurring local contraction provides information about the heart (2), which can be used for a better and/or more reliable characterization of the heart (2).

13 Claims, 8 Drawing Sheets

APPARATUS, METHOD AND COMPUTER PROGRAM FOR DETERMINING A PROPERTY OF A HEART

FIELD OF THE INVENTION

The present invention relates to an apparatus, a method and a computer program for determining a property of a heart.

BACKGROUND OF THE INVENTION

Apparatuses for determining a property of a heart are used, for example, in the field of interventional treatment for atrial fibrillation. During the interventional procedure cardiac tissue is denaturized by applying energy. For example, in radio frequency (RF) catheter ablation radio frequency energy is applied to the cardiac tissue by an ablation catheter, wherein due to resistive losses in the tissue the myocardium is heated up and the heated muscle cells in the cardiac tissue die off and lose their biological function. Since the optimal parameters for ablation, such as power and duration, vary largely due to sizeable intra- and inter-patient differences in thickness of the local heart wall, perfusion, blood pressure, etc., it is important to be able to monitor the progress of the lesion development in the tissue and, preferentially, the depth of the lesion with respect to the thickness of the tissue at the treatment site, to prevent damages to the patient caused by underheating or overheating of the ablation site. Ablation catheters that are used in practice therefore provide feedback about properties of the heart, including, for example, local conduction (electrograms), tissue impedance and/or temperature.

US 2004/0181139 A1 discloses an apparatus for determining a property of a heart. The apparatus comprises a catheter for electrical ablation of a vessel/heart and for monitoring the quality of the lesion by determining the tissue impedance or the electrical signal strength at the ablation site. These local properties of the heart, however, only provide limited information about the progress of the lesion and, in particular, about the depth of the lesion with respect to the thickness of the tissue at the treatment site.

SUMMARY OF THE INVENTION

It is an object of the present invention to provide an apparatus, a method and a computer program for determining a property of a heart, which provides further information about the heart, which can be used for a better and/or more reliable characterization of the heart.

In an aspect of the present invention an apparatus for determining a property of a heart is presented, wherein the apparatus comprises:

a catheter comprising a first property sensing unit for sensing a contraction signal indicative of a reoccurring local contraction of the heart at a sensing site of the heart and a first property determining unit for determining the reoccurring local contraction of the heart at the sensing site from the sensed contraction signal as a first property of the heart.

Since the first property sensing unit is comprised by a catheter and adapted to sense the contraction signal at the sensing site and since the first property determining unit determines the reoccurring local contraction of the heart at the sensing site from the sensed contraction signal, the reoccurring local contraction can be determined locally at the sensing site within a heart of a person or of an animal. This allows for a better and/or more reliable characterization of the heart in particular, for a better and/or more reliable appraisal of the behavior of the heart.

Preferentially, the catheter is an ablation catheter and/or a diagnostic catheter. Moreover, the heart can be a complete heart, for example, an entire heart of a person, or it can be only a part of a heart, such as a ventricle or atrium or simply a confined region of cardiac tissue.

The term "reoccurring local contraction" denotes that the contraction of the heart at the sensing site is a contraction that occurs repeatedly, that is, it occurs more than just once. Moreover, the term also denotes that the contraction occurs locally at the sensing site, which means that it is not the global contraction performed by the heart for pumping blood through the blood vessels. Furthermore, the considered "reoccurring local contraction" is autonomous, that is, it is not induced, for example, by applying energy to the heart, but it is caused by the functional behavior of the heart itself. Preferentially, the reoccurring local contraction of the heart at the sensing site is periodic or substantially periodic, for example, if the heart is a heart of a person suffering from atrial fibrillation, the inter-contraction period, that is, the period between two subsequent reoccurring local contractions of the heart at the sensing site is related to, in particular, may be equal to, the atrial fibrillation cycle length. Moreover, if the reoccurring local contraction of the heart at the sensing site is periodic or substantially periodic, the period of the reoccurring local contraction itself may change over time, for example, the period may become shorter or longer.

The term "sensing site" denotes a confined region or spot of the heart for which a contraction signal that is indicative of the reoccurring local contraction of the heart in that confined region or at that spot is sensed.

The contraction signal is preferentially sensed at a plurality of points in time (sampling instances) with a sampling rate that is higher than twice the bandwidth of the reoccurring local contraction of the heart at the sensing site. This makes it possible to avoid—at least to some extent—errors or inaccuracies in the determination of the reoccurring local contraction caused by aliasing effects. In an alternative, the contraction signal may also be sensed continuously over time, in which case it may subsequently be converted to a time-discrete representation for further processing.

Preferentially, the reoccurring local contraction of the heart at the sensing site of the heart is determined based on temporal changes of the sensed contraction signal.

The present invention may be used, for example, in the field of cardiac ablation for treatment of atrial fibrillation, where the activation of cardiac tissue by an electrical impulse triggers intracellular events, including changes in calcium level, resulting in a (intracellular calcium-dependent) reoccurring local contraction of cardiac muscle cells. This effect is known as "excitation-contraction coupling". Providing the clinician with information about such reoccurring local contractions and the changes therein may allow him/her to better and/or more reliable appraise the behavior of the heart in response to electrical impulses.

For example, during a successful cardiac ablation procedure the atrial fibrillation cycle length usually increases (indicating that the tissue substrate becomes less arrhythmogenic) due to a reduction in circulating wavelets. This behavior may be monitored by measuring local electrical activation, however, electrograms are usually very difficult to interpret and may not always be accurate due to disturbances caused, for example, by far-field potentials or radio frequency noise. Since the gradual increase in atrial fibrillation cycle length may also be reflected by an increase in the period and/or the force of the reoccurring local contraction at the ablation site, the determination of the reoccurring local contraction of the heart at the ablation site may facilitate an improved monitoring of the progress of the electrical isolation of the arrhythmogenic substrate and the lesion development in the tissue and, preferentially, of the depth of the lesion with respect to the thickness of the tissue at the treatment site.

Additionally or alternatively, the determination of a reoccurring local contraction of the heart at a sensing site may help to identify dissociation of excitation-contraction coupling, that is, the case where an electrical pulse in the cardiac tissue at the sensing site does not result in a local contraction at the sensing site, or to localize non-contracting scar tissue. A dissociation of excitation-contraction coupling can, for example, be identified by comparing the determined contraction at the sensing site with an electrical signal which might also be detected at the sensing site. If an electrical signal is detected at the sensing site, which is not followed by a contraction at the sensing site, a dissociation of excitation-contraction coupling is detected. For example, a temporal threshold can be predefined, wherein, if the temporal distance between the detection of an electrical signal and a local contraction is larger than the predefined temporal threshold, it is determined that a dissociation of excitation-contraction coupling is present at the sensing site. The identification of the location of ventricular scar tissue from determined reoccurring local contractions of the heart may help, for example, in finding a suitable spot for the positioning of pacemaker lead electrodes.

It is preferred that the first property determining unit is adapted to determine a periodicity and/or phase of the reoccurring local contraction. For example, the first property determining unit can be adapted to determine the periodicity and/or the phase of the contraction signal as the periodicity and/or phase, respectively, of the reoccurring local contraction. The phase is preferentially determined with respect to a reference. The reference is, for example, a reoccurring local contraction determined for a certain point in time. If an ablation procedure is performed, the reference is, for example, the reoccurring local contraction immediately before starting the ablation procedure. For example, the determination of the periodicity and/or phase of the reoccurring local contraction of the heart at the sensing site of the heart (and the temporal changes therein) during an ablation procedure can be used to monitor the progress of the electrical isolation of the arrhythmogenic substrate and the lesion development in the cardiac tissue and, preferentially, the depth of the lesion with respect to the thickness of the cardiac tissue at the treatment site, as will be described in more detail further below.

Preferentially, the periodicity and/or phase of the reoccurring local contraction is determined with a high accuracy, preferentially with an accuracy of about 50 ms or higher, more preferentially with an accuracy of about 10 ms or higher, even more preferentially with an accuracy of about 5 ms or higher.

It is further preferred that the apparatus comprises a reference signal providing unit for providing a reoccurring reference signal and that the first property determining unit is adapted to determine the periodicity and/or phase of the reoccurring local contraction with respect to the reoccurring reference signal. This allows determining a relationship that may exist between the reoccurring reference signal and the reoccurring local contraction of the heart at the sensing site. It is thereby preferred that the reference signal providing unit is adapted to provide a reoccurring reference signal that is dependent on an attribute of the heart. For example, the reference signal providing unit may be an electrocardiograph for measuring an ECG (electrocardiogram) signal representing the heart rate and rhythm as the reoccurring reference signal. The determination of the periodicity and/or phase of the reoccurring local contraction of the heart at the sensing site with respect to the measured ECG signal then allows determining the relationship between the cardiac cycle and the reoccurring local contraction. In particular, if the reoccurring local contraction is determined at different sensing sites of the heart, the knowledge about the relationship between the cardiac cycle and the reoccurring local contraction at the different sensing sites makes it possible to determine the sequence in which different parts of the heart are activated.

Preferentially, the first property determining unit is adapted to determine an amplitude of the reoccurring local contraction. Determining the amplitude, that is, the force of the reoccurring local contraction of the heart at the sensing site of the heart, allows providing further information about the heart that may allow for a better and/or more reliable characterization of the heart. For example, the determination of the amplitude of the reoccurring local contraction of the heart at the sensing site of the heart (and the temporal changes therein) during an ablation procedure may further facilitate monitoring the progress of the electrical isolation of the arrhythmogenic substrate and the lesion development in the cardiac tissue and, preferentially, the depth of the lesion with respect to the thickness of the cardiac tissue at the treatment site, as will be explained in more detail further below.

It is preferred that the first property determining unit is adapted to determine the reoccurring local contraction based on temporal changes of the sensed contraction signal. This allows for a simple determination of the reoccurring local contraction of the heart at the sensing site. For example, if the contraction signal is sensed at a plurality of points in time (sampling instances) or, alternatively, if it is converted to a time-discrete representation after it has been sensed continuously over time, the reoccurring local contraction of the heart at the sensing site may be determined based on the changes of the contraction signal between subsequent points in time. These temporal changes of the contraction signal between subsequent points in time are preferentially quantified by calculating a difference between the sampling values of the contraction signal at neighboring points in time or by calculating a correlation.

In particular, it is preferred that the first property sensing unit is adapted to sense the contraction signal at different points in time and that the first property determining unit is adapted to apply a similarity measure for comparing the sensed contraction signal at neighboring points in time resulting in similarity values indicating the similarity of the sensed contraction signal at the neighboring points in time, to determine non-similarity points in time by comparing the similarity values to a threshold, and to determine at least one of the periodicity and the phase of the reoccurring local contraction of the heart from the determined non-similarity points in time.

Preferentially, the first property sensing unit is an acoustic sensing unit for emitting acoustic waves for being reflected at one or more depths within the heart and for receiving the reflected acoustic waves, wherein the sensed contraction signal depends on the received acoustic waves. Acoustic sensing can be used for sensing a heart and, in particular, for sensing a heart at different depths within the cardiac tissue. The acoustic sensing of a contraction signal that depends on received acoustic waves reflected at one or more depths within the cardiac tissue provides sufficient information about the heart at the sensing site to make it possible to determine the reoccurring local contraction of the heart at the sensing site with a high quality.

Preferentially, the frequency of the acoustic waves used for the acoustic sensing of the heart is greater than 20 MHz in order to provide a spatial resolution that allows for a high-quality determination of the reoccurring local contraction of the heart at the sensing site of the heart.

It is preferred that the acoustic sensing unit comprises an ultrasound transducer, which may be a single element ultrasound transducer or an ultrasound transducer array (each with or without a fluid lens). For example, if the first property sensing unit comprises a single element ultrasound transducer, the acoustic sensing unit may emit a single beam of ultrasound waves and sense a contraction signal representing reflections of the ultrasound waves reflected at one or more depths within the cardiac tissue. The contraction signal corresponding to a point in time can be regarded as an 'A-line', which represents the amplitude of the reflections as a function of the time required for the return of the reflected ultrasound waves, and, thus, the depth of the reflecting cardiac tissue with respect to the ultrasound transducer.

By sensing the contraction signal at a plurality of points in time (sampling instances) or, alternatively, by converting it to a time-discrete representation after it has been sensed continuously over time, a plurality of 'A-lines' are acquired which can be stacked together to obtain a matrix. The reoccurring local contraction of the heart at the sensing site may then be determined by analyzing the changes between subsequent 'A-lines' of this matrix. In particular, a similarity measure for comparing the sensed contraction signal at neighboring points in time may be applied, resulting in similarity values indicating the similarity of the sensed contraction signal at the neighboring points in time and non-similarity points in time may be determined by comparing the similarity values to a threshold. From the determined non-similarity points in time, the periodicity and/or phase of the reoccurring local contraction of the heart may then be determined.

As an alternative to an acoustical sensing, the first property sensing unit can also use another imaging modality. For example, the first property sensing unit can be an optical sensing unit using optical imaging with, for example, visible or infrared light from a laser or from another light source. Thus, instead of an acoustic sensing unit an optical sensing unit emitting and receiving, for example, infrared light may be used as the first property sensing unit, wherein the contraction signal represents reflections of the infrared light reflected at different depths within the heart.

It is preferred that the catheter comprises a further property sensing unit for sensing a property signal indicative of a further property of the heart at the sensing site and that the apparatus comprises a further property determining unit for determining the further property of the heart at the sensing site from the sensed property signal. This makes it possible to provide further information about a heart that may allow for a better and/or more reliable characterization of the heart. For example, the further property sensing unit and the further property determining unit may be adapted to determine an electrical property like the local conduction (electrograms) and/or tissue impedance of the heart at the sensing site. Additionally or alternatively, the further property sensing unit may comprise, for example, a temperature sensor for sensing a temperature signal indicative of a temperature of the heart at the sensing site and the further property determining unit may be adapted to determine the temperature of the heart at the sensing site from the sensed temperature signal.

Preferentially, the catheter comprises an energy applying unit for applying energy to the heart. A catheter comprising an energy applying unit for applying energy to the heart makes it possible to apply a treatment to the heart. For example, the catheter may preferentially be used for performing an ablation procedure for the treatment of atrial fibrillation. The energy applying unit preferentially comprises an electrode for applying radio frequency energy to the cardiac tissue, but it may also utilize other known energy applying methods, such as cooling or cauterizing. Preferentially, the energy applying unit is adapted for applying energy to the heart at the sensing site.

It is preferred that the energy applying unit is adapted to ablate the heart and that the apparatus comprises an ablation progress determining unit for determining a progress of ablation based on the determined reoccurring local contraction. For example, the progress of the electrical isolation of the arrhythmogenic substrate and the lesion development in the cardiac tissue and, preferentially, the depth of the lesion with respect to the thickness of the cardiac tissue at the treatment site, may be determined based on a periodicity and/or phase and/or amplitude of the determined reoccurring local contraction. For example, in an embodiment, it is assumed that with progressing ablation the amplitude of the determined reoccurring local contraction decreases. A certain decrease of the amplitude can then be correlated with a certain ablation progress, for example, by calibration measurements. Moreover, in an embodiment, it is assumed that an increasing period of the determined reoccurring local contraction indicates an increasing progression of ablation. A certain increase of the period can therefore be correlated with a certain ablation progress. In particular, the ablation progress determining unit can be calibrated such that an increase of a period of the determined reoccurring local contraction and/or a decrease of the amplitude indicates the depth in the cardiac tissue, to which the ablation has been progressed. Generally, if ablation progresses, the periodicity and/or the phase and/or the amplitude of the determined reoccurring local contraction is modified. Preferentially, by calibration measurements or by known relations between a progression of ablation and a modification of the determined reoccurring local contraction the ablation progress determining unit is adapted to determine a progress of ablation based on a modification of the periodicity and/or phase and/or amplitude of the determined reoccurring local contraction. Moreover, in an embodiment the periodicity and/or phase and/or amplitude of the reoccurring local contraction is determined at the sensing site of the heart for different depths within the cardiac tissue, wherein the individual behavior of these values at the different depths can be further utilized to determine the ablation progress at the sensing site.

Preferentially, the apparatus comprises a position determining unit for determining a position of the sensing site. This allows determining a relationship that may exist between the anatomy of the heart and the position of the sensing site of the heart for which the reoccurring local contraction of the heart is determined. The position of the sensing site may be determined, for example, using electrical or magnetic localization or GPS (Global Positioning System). For instance, the catheter can be provided with elements being visible in an external imaging system for determining the position of the catheter, in particular, of the catheter tip. In an embodiment, the catheter tip can comprise a localization coil, wherein the position of the localization coil, and, thus, of the catheter can be determined within a magnetic resonance imaging system.

In particular, if the reoccurring local contraction of the heart is determined at different sensing sites of the heart and the positions of the different sensing sites are determined, these determined positions make it possible to determine similarities, variations and/or other characteristics of the reoccurring local contraction of the heart at the different sensing sites in dependence of the positions of the different sensing sites.

Preferentially, the position of the sensing site is determined with respect to a reference frame. Such a reference frame may be, for example, a local or global, two- or three-dimensional coordinate system (with which a model of the heart may be registered) or a two- or three-dimensional model or map of the heart providing anatomical information about the heart. For example, the reference frame may be a global tree-dimensional coordinate system with which a three-dimensional model of the heart is registered or it may itself be a three-dimensional anatomical model of the heart.

It is further preferred that the first property sensing unit and the first property determining unit are adapted to determine the reoccurring local contraction at different sensing sites of the heart, that the position determining unit is adapted to determine the positions of the different sensing sites, that the apparatus further comprises a map generation unit for generating a contraction map of the heart based on the determined reoccurring local contraction at the different sensing sites and the determined positions of the different sensing sites, and that the contraction map represents the reoccurring local contraction at the positions of the different sensing sites.

Such a contraction map allows providing information about the heart that may allow for a better and/or more reliable appraisal of a behavior of the heart. For example, a contraction map of the heart may help to identify dissociation of excitation-contraction coupling, that is, the case where an electrical pulse in the cardiac tissue at the sensing site does not result in a local contraction at the sensing site, or to localize non-contracting scar tissue. The identification of the location of ventricular scar tissue from determined local contraction patterns may help, for example, in finding a suitable spot for the positioning of pacemaker lead electrodes.

It is further preferred that the catheter comprises a further property sensing unit for sensing a property signal indicative of a further property of the heart at the sensing site, wherein the apparatus comprises a further property determining unit for determining the further property of the heart at the sensing site from the sensed property signal, wherein the further property sensing unit and the further property determining unit are adapted to additionally determine the further property at the different sensing sites of the heart, and wherein the map generation unit is adapted to generate a contraction map of the heart which additionally represents the further property at the positions of the different sensing sites based on the determined further property at the different sensing sites and the determined positions of the different sensing sites.

A contraction map that additionally represents a further property of the heart makes it possible to provide further information about the heart that may allow for a better and/or more reliable characterization of the heart.

In a further aspect of the present invention a method for determining a property of a heart is provided, wherein the method comprises the following steps:

sensing a contraction signal indicative of a reoccurring local contraction of the heart at a sensing site of the heart by means of a first property sensing unit comprised in a catheter and determining the reoccurring local contraction of the heart at the sensing site from the sensed contraction signal as a first property of the heart by means of a first property determining unit.

In a further aspect of the present invention a computer program for determining a property of a heart is provided, wherein the computer program comprises program code means for causing a computer to carry out the steps of the aforementioned method, when the computer program is run on a computer controlling the aforementioned apparatus.

In a further aspect of the present invention a contraction map of a heart is provided, the contraction map representing a reoccurring local contraction of the heart at different positions of sensing sites of the heart. Preferentially, the contraction map is generated based on the reoccurring local contraction at the different sensing sites and the determined positions of the different sensing sites. The positions of the different sensing sites are preferentially determined by a position determining unit and the reoccurring local contraction is preferentially determined at the different sensing sites by a first property determining unit from a contraction signal indicative of the reoccurring local contraction of the heart. Preferentially, the contraction signal is sensed by a first property sensing unit comprised by a catheter.

It shall be understood that the aforementioned apparatus, the aforementioned method, the aforementioned computer program, and the aforementioned contraction map have similar and/or identical preferred embodiments, in particular, as defined in the claims.

It shall be understood that preferred embodiments of the invention can also be any combination of the dependent claims with a respective independent claim.

BRIEF DESCRIPTION OF THE DRAWINGS

These and other aspects of the invention will be apparent from and elucidated with reference to the embodiments described hereinafter. In the following drawings

DETAILED DESCRIPTION OF EMBODIMENTS

Figure 1:
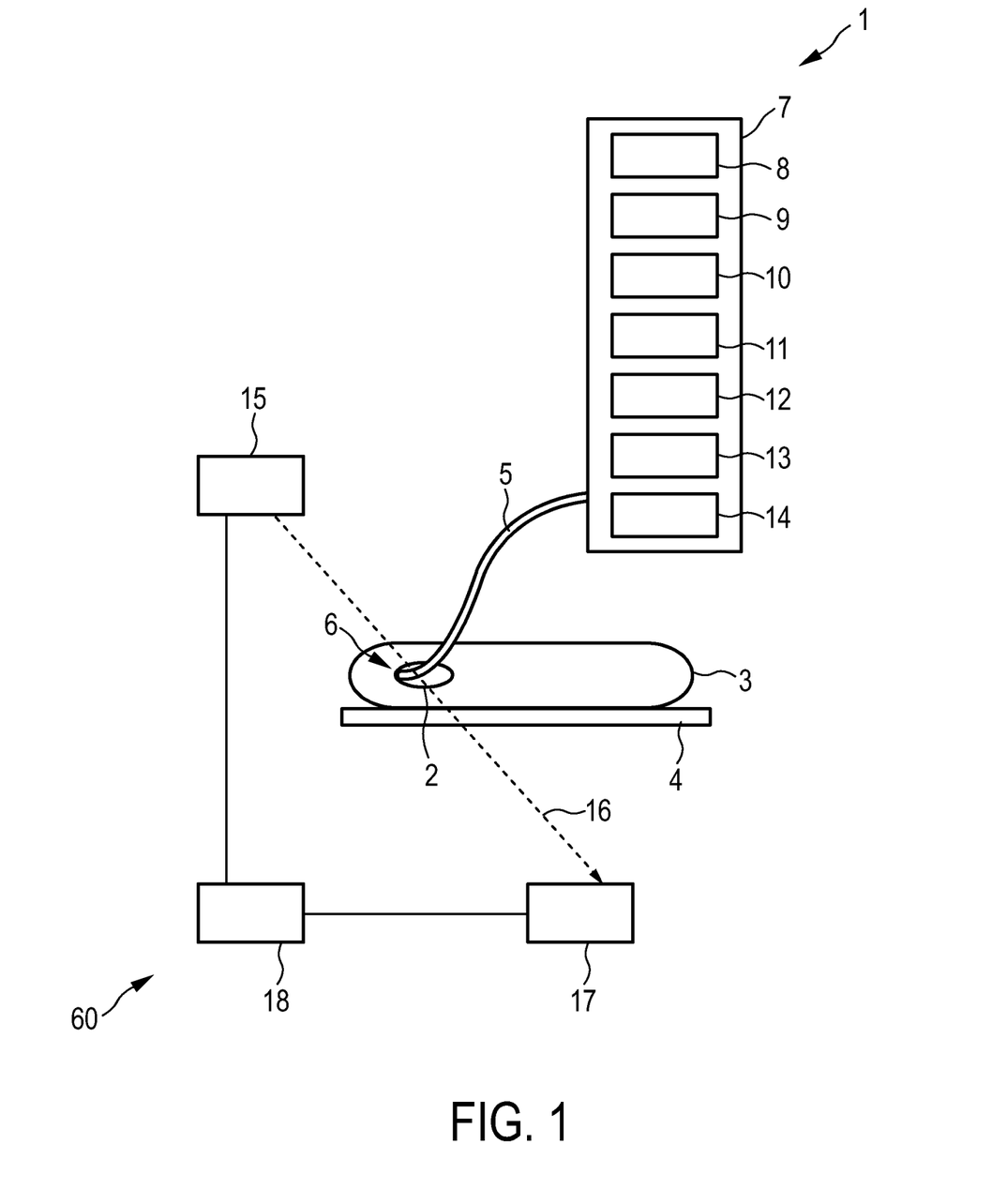
FIG. 1 shows schematically and exemplarily an embodiment of an apparatus for determining a property of a heart.

FIG. 1 shows schematically and exemplarily an apparatus 1 for determining a property of a heart 2 of a patient 3. The patient 3 is located on a patient table 4. The apparatus 1 comprises a catheter 5 comprising a first property sensing unit for sensing a contraction signal indicative of a reoccurring local contraction of the heart 2 at a sensing site of the heart 2. In this embodiment, the first property sensing unit is located at a distal end 6 of the catheter 5. The distal end 6 of the catheter 5 comprising the first property sensing unit will be described in more detail further below.

The apparatus 1 for determining a property of a heart 2 further comprises a catheter control unit 7, which comprises a first property determining unit 8 for determining the reoccurring local contraction of the heart 2 at the sensing site from the contraction signal as a first property of the heart 2.

The catheter control unit 7 further comprises a guiding control unit 9 for guiding the distal end 6 of the catheter 5 to the sensing site of the heart 2. The guiding control unit 9, in this embodiment, controls build-in guiding means (not shown in FIG. 1) of the catheter 5. In another embodiment, the catheter 5 can, for example, also be steered and navigated by the use of steering-wires in order to passively guide the distal end 6 of the catheter 5 to the desired location within the heart 2. Also, the steering-wires can be controlled by the guiding control unit 9. Alternatively, a magnetic or other guiding of the distal end 6 of the catheter 5 to the sensing site of the heart 2 can be employed.

During the guidance of the distal end 6 of the catheter 5 to the sensing site of the heart 2 and preferentially also during the sensing of the contraction signal a fluoroscopy device 60 images the position of the distal end 6 of the catheter 5 within the patient 3 and, in particular, within the heart 2. The fluoroscopy device 60 comprises an X-ray source 15, which generates an X-ray beam 16, which is schematically shown in FIG. 1, for traversing a region of the patient 3, in which the catheter 5, in particular, the distal end 6 of the catheter 5, is present. After the X-ray beam 16 has traversed the patient 3, the X-ray beam 15 is detected by an X-ray detector 17. The X-ray source 15 and the X-ray detector 17 are controlled by a fluoroscopy control unit 18, which preferentially also comprises a display for showing a fluoroscopy image.

In another embodiment, instead of a fluoroscopy device, another imaging device, for example, a magnetic resonance imaging device, an ultrasonic imaging device or a computed tomography imaging device, can be used for imaging the position of the distal end 6 of the catheter 5 within the patient 3 and, in particular, within the heart 2.

Figure 2A:
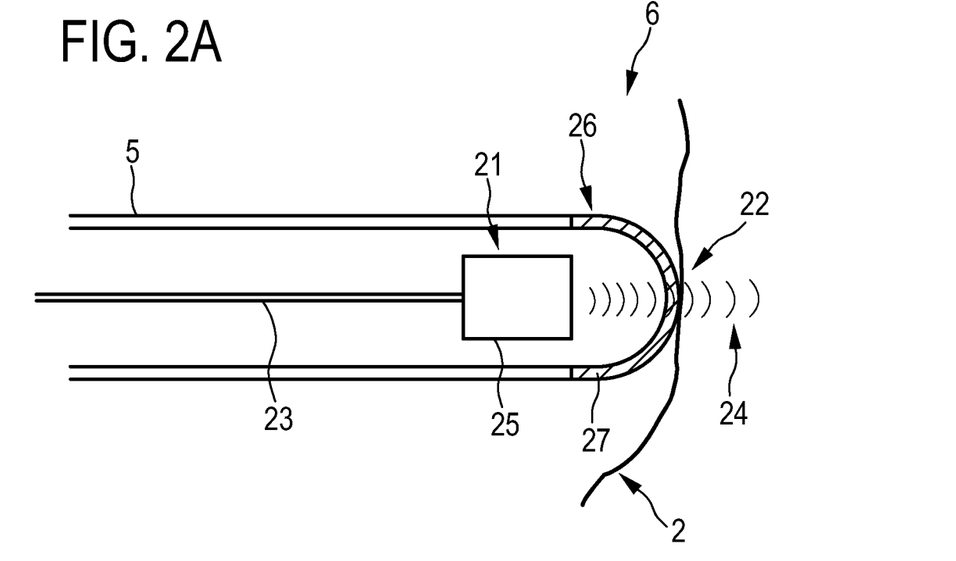
FIGS. 2A, 2B show schematically and exemplarily two embodiments of a distal end of a catheter for use in an apparatus for determining a property of a heart.

FIG. 2A shows schematically and exemplarily an embodiment of a distal end 6 of a catheter 5 for use in an apparatus 1 for determining a property of a heart 2. Similar reference signs in the figures indicate similar elements.

In the embodiment shown in FIG. 2A, the catheter 5 comprises a first property sensing unit 21 for sensing a contraction signal indicative of a reoccurring local contraction of the heart 2 at a sensing site 22 of the heart 2. The first property sensing unit 21 is connectable to the first property determining unit 8, shown in FIG. 1, via a connection 23 suitable for conveying the contraction signal from the first property sensing unit 21 to the first property determining unit 8. The connection 23 can be, for example, an electrical connection or an optical connection.

In this embodiment, the first property sensing unit 21 is an acoustic sensing unit for emitting acoustic waves 24 for being reflected at one or more depths within the heart 2 and for receiving the reflected acoustic waves 24. The sensed contraction signal depends on the received acoustic waves 24. In another embodiment, the first property sensing unit 21 can also use another imaging modality. For example, the first property sensing unit 21 can be an optical sensing unit using optical imaging with, for example, visible or infrared light from a laser or from another light source. Thus, instead of an acoustic sensing unit an optical sensing unit emitting and receiving, for example, infrared light may be used as the first property sensing unit 21, wherein the contraction signal represents reflections of the infrared light reflected at different depths within the heart 2.

The first property sensing unit 21, which in this embodiment is an acoustic sensing unit, comprises an ultrasound transducer 25, in particular, in this embodiment, a single element ultrasound transducer 25. Such a single element ultrasound transducer is capable of emitting and receiving a beam of ultrasound waves, that is, acoustic waves 24. In another embodiment, the first property sensing unit 21 can further comprise a liquid lens or the ultrasound transducer 25 can be an ultrasound transducer array. The use of a single element ultrasound transducer with a liquid lens or of an ultrasound transducer array makes it possible to sense the heart 2 over a larger sensing range. In another embodiment, the first property sensing unit 21 can also comprise several ultrasound transducers, that is, the first property sensing unit 21 can comprise a single ultrasound transducer or several ultrasound transducers.

In order to allow for the transmission of the acoustic waves 24, in particular, the ultrasound waves 24, the catheter 5 is preferentially filled with a transmission medium like a solid or a fluid (not shown in FIG. 2A), for example a cooling fluid or other fluid.

In the embodiment shown in FIG. 2A, the catheter 5 comprises an energy applying unit 26 for applying energy to the heart 2. The energy applying unit 26 comprises a catheter electrode 27, in particular, in this embodiment, a radio frequency catheter electrode 27, which is connectable to an electrical energy source 10 comprised by the catheter control unit 7, shown in FIG. 1, of the apparatus 1 for determining a property of a heart 2, via a contact lead (not shown in FIG. 2A). Thus, electrical energy, in this embodiment, radio frequency energy, can be applied to the heart 2 via the energy applying unit 26 of the catheter 5. The catheter electrode 27, in particular, in this embodiment, the radio frequency catheter electrode 27, is an acoustically transparent electrode, for example, a TPX electrode with a thin metallic coating on the frontside or an electrode made of another acoustically transparent material such as doped polymer. In another embodiment, the energy applying unit 26 can also use another energy source, such as laser, cryothermy, high intensity ultrasound or microwaves.

In this embodiment, the energy applying unit 26 is adapted to ablate the heart 2. The apparatus 1, in particular, the catheter control unit 7, comprises an ablation progress determining unit 11, shown in FIG. 1, for determining a progress of ablation based on the determined reoccurring local contraction of the heart 2 at the sensing site 22 of the heart 2. Preferentially, a periodicity and/or phase and/or amplitude of the determined reoccurring local contraction is used to determine the progress of ablation. For example, in an embodiment, it is assumed that with progressing ablation the amplitude of the determined reoccurring local contraction decreases. A certain decrease of the amplitude can then be correlated with a certain ablation progress, for example, by calibration measurements. Moreover, in an embodiment, it is assumed that an increasing period of the determined reoccurring local contraction indicates an increasing progression of ablation. A certain increase of the period can therefore be correlated with a certain ablation progress. In particular, the ablation progress determining unit can be calibrated such that an increase of a period of the determined reoccurring local contraction and/or a decrease of the amplitude indicates the depth in the cardiac tissue, to which the ablation has been progressed. Generally, if ablation progresses, the periodicity and/or the phase and/or the amplitude of the determined reoccurring local contraction is modified. Preferentially, by calibration measurements or by known relations between a progression of ablation and a modification of the determined reoccurring local contraction the ablation progress determining unit is adapted to determine a progress of ablation based on a modification of the periodicity and/or phase and/or amplitude of the determined reoccurring local contraction. Moreover, it the periodicity and/or phase and/or amplitude of the reoccurring local contraction is determined at the sensing site of the heart for different depths within the cardiac tissue, the individual behavior of these values at the different depths can be further utilized to determine the ablation progress at the sensing site.

Figure 2B:
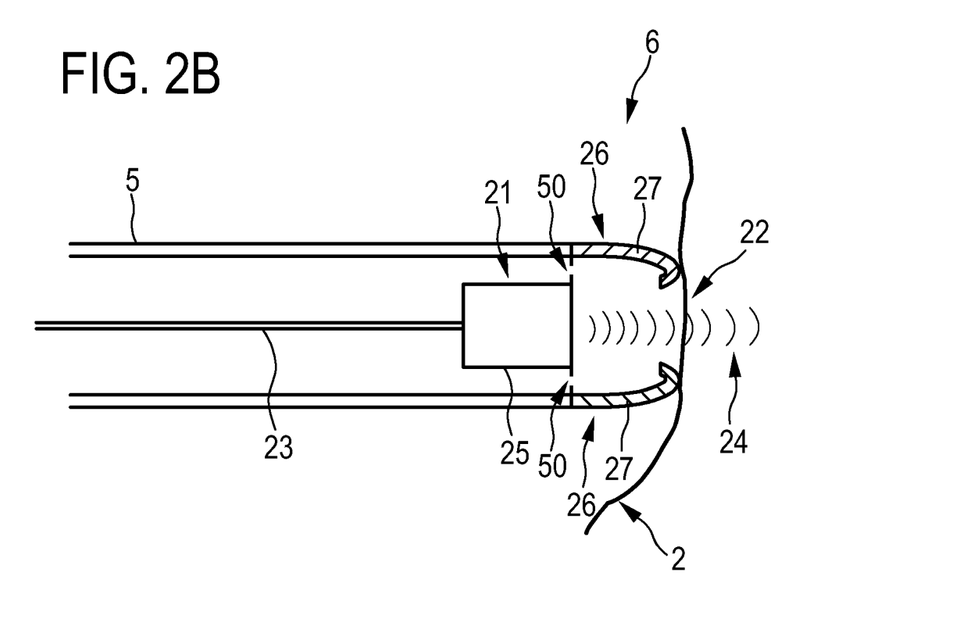

FIG. 2B shows schematically and exemplarily a further embodiment of a distal end 6 of a catheter 5 for use in an apparatus 1 for determining a property of a heart 2.

In the embodiment shown in FIG. 2B, the catheter 5 differs from the one shown in FIG. 2A in that the catheter electrode 27, in particular, in this embodiment, the radio frequency catheter electrode 27, comprised by the energy applying unit 26, is an annular electrode. The annular catheter electrode 27 and the first property sensing unit 21 together form a kind of channel through which the acoustic waves 24 are transmitted. In order to avoid the presence of air and/or blood in front of the first property sensing unit 21, the channel is preferentially filled with an irrigation fluid (not shown in FIG. 2B), for example, a saline solution, that is pumped through the lumen of the catheter 5 and that can leave the lumen through openings 50. The lumen can be completely filled by the irrigation fluid or a tube can be present within the lumen of the catheter 5, wherein the tube is connected to the openings 50 such that the irrigation fluid can leave the catheter 5 through the openings 50.

Figure 3:
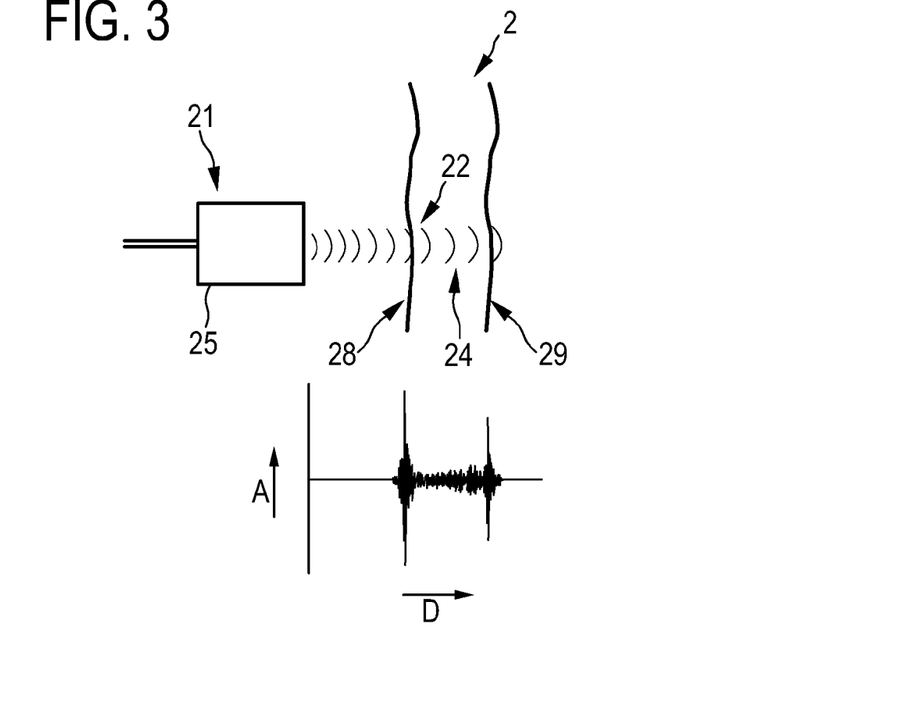
FIG. 3 shows schematically and exemplarily the sensing of a contraction signal indicative of a reoccurring local contraction of a heart at a sensing site of the heart by a first property sensing unit.

FIG. 3 shows schematically and exemplarily the sensing of a contraction signal indicative of a reoccurring local contraction of a heart 2 at a sensing site 22 of the heart 2 by a first property sensing unit 21.

The first property sensing unit 21, which in this embodiment is an acoustic sensing unit, emits and receives acoustic waves 24 and the sensed contraction signal represents reflections of the acoustic waves 24 reflected at one or more depths within the heart 2. The sensed contraction signal corresponding to a point in time is visualized in FIG. 3 as a two-dimensional 'A-mode' image, in which the horizontal axis D of the image represents the time required for the return of the emitted and reflected acoustic waves 24 and, thus, the depth of the reflecting cardiac tissue with respect to the first property sensing unit 21, and in which the vertical axis A represents the amplitude of the reflections. Alternatively, the same information can also be visualized as a one-dimensional 'B-mode' image, in which the one axis of the image represents the depth of the reflecting cardiac tissue with respect to the first property sensing unit 21 and in which the amplitude of the reflections is encoded as a brightness value. The contraction signal shown in FIG. 3 features noticeable peaks at a front wall 28 and a back wall 29 of the heart 2. The smaller peaks in between the front wall 28 and the back wall 29 reflect the inhomogeneity of the cardiac tissue.

Figure 4:
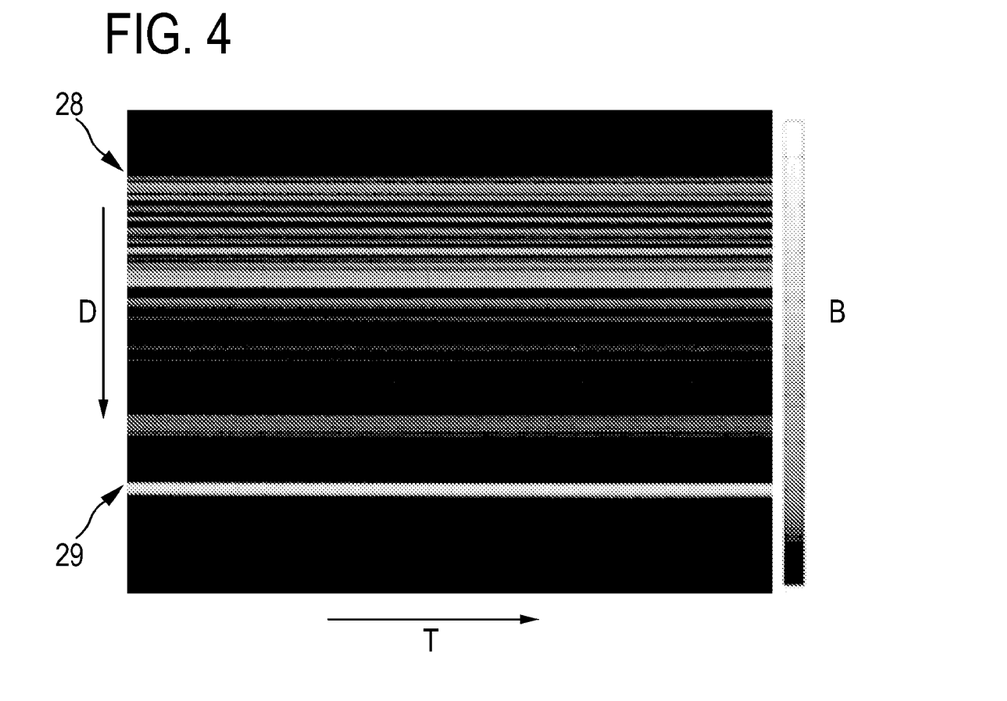
FIG. 4 shows schematically and exemplarily the temporal behavior of a contraction signal indicative of a reoccurring local contraction of a heart sensed at a sensing site of the heart by a first property sensing unit, FIGS. 5A to 5C serve to illustrate the determination of a reoccurring local contraction of a heart at a sensing site of the heart from a sensed contraction signal.

FIG. 4 shows schematically and exemplarily the temporal behavior of a contraction signal indicative of a reoccurring local contraction of a heart 2 sensed at a sensing site 22 of the heart 2 by a first property sensing unit 21.

In this embodiment, the temporal behavior of the contraction signal is visualized in FIG. 4 as a two-dimensional 'M-mode' image, in which the horizontal axis T of the image represents the time, in which the vertical axis D of the image represents the depth of the reflecting cardiac tissue with respect to the first property sensing unit 21, which should be considered to be located at the top of the image, and in which the amplitude of the reflections is encoded as a brightness value B. The two-dimensional 'M-mode' image is generated, in this embodiment, by first sensing the contraction signal at a plurality of points in time at a sampling frequency of 20 Hz. In another embodiment, the contraction signal can also be converted into a time-discrete representation after it has been sensed continuously over time. Moreover, if required, a higher sampling frequency, for example, greater than 100 Hz, may also be used. The contraction signal corresponding to each point in time ('A-line') is preferentially filtered using, for example, a Hilbert filter, and the absolute amplitudes after filtering are converted into one-dimensional 'B-mode' images which are stacked together to obtain the two-dimensional 'M-mode' image.

Since in the situation shown in FIGS. 3 and 4, the heart 2 does not exhibit a reoccurring local contraction at the sensing site 22 and since the first property sensing unit 21 remained at a fixed position with respect to the heart 2 during the sensing of the contraction signal, the 'B-lines' corresponding to different points in time do not change in the two-dimensional 'M-mode' image resulting in a 'stripe-like' image in which the front wall 28 and the back wall 29 are clearly recognizable.

Figure 5A:
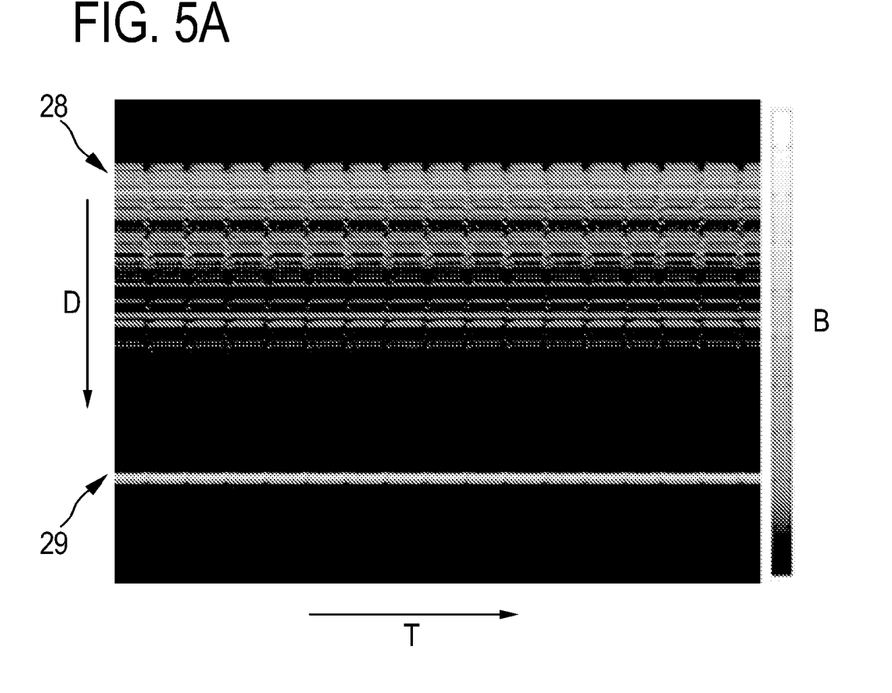
Figure 5B:
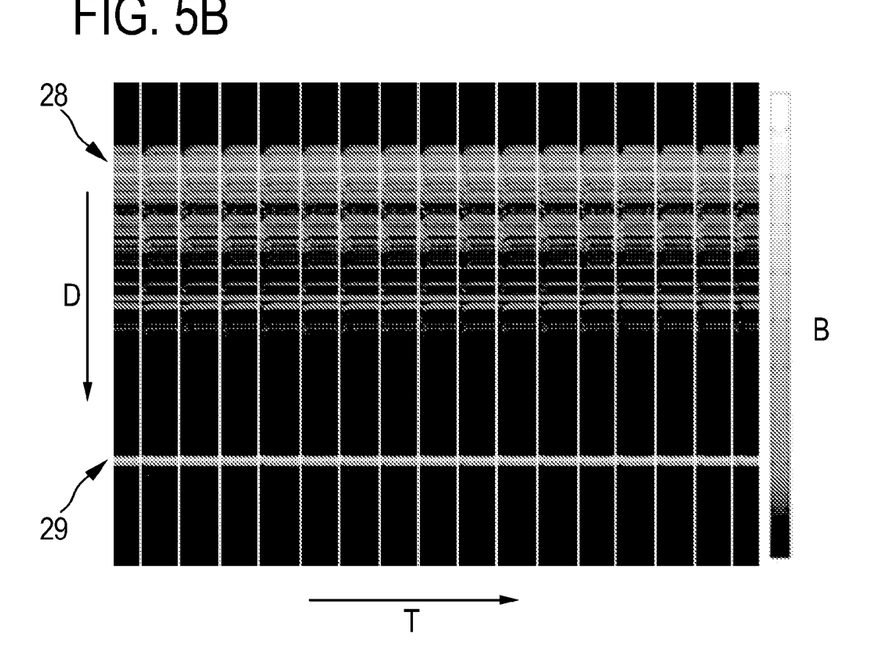
Figure 5C:
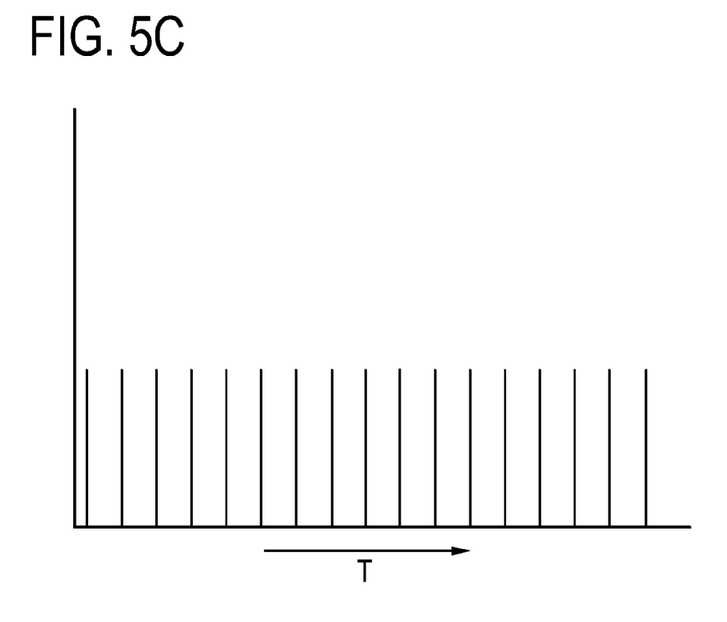

FIGS. 5A to 5C show a situation in which the heart 2 exhibits a reoccurring local contraction at a sensing site 22 of the heart 2. They serve to illustrate the determination of the reoccurring local contraction of the heart 2 at the sensing site 22 of the heart 2 from a sensed contraction signal.

FIG. 5A shows the temporal behavior of a contraction signal indicative of a reoccurring local contraction of a heart 2 sensed at a sensing site 22 of the heart 2 by a first property sensing unit 21. The contraction signal is visualized as a two-dimensional 'M-mode' image as described with reference to FIG. 4. Since the heart 2, in this embodiment, exhibits a reoccurring local contraction at the sensing site 22, a corresponding reoccurring local displacement of the cardiac tissue can be recognized in the two-dimensional 'M-mode' image. The contraction signal has been sensed, in this embodiment, with the distal end 6 of the catheter 5 not being in direct contact with the heart 2

The reoccurring local contraction of the heart 2 at the sensing site 22 of the heart 2 is determined based on the temporal changes of the sensed contraction signal by the first property determining unit 8 shown in FIG. 1. In this embodiment, the reoccurring local contraction is determined as follows.

The individual 'A-lines' corresponding to the sensed contraction signal at the plurality of points in time are stacked together to form a matrix A. The matrix A is composed of column vectors $A_1, A_2, \ldots, A_N$, where $A_n$, with $n \in [1, \ldots, N]$, is an 'A-line' with elements $A_{n1}, A_{n2}, \ldots, A_{nM}$, where $A_{nm}$, with $m \in [1, \ldots, M]$, is the amplitude of the reflection of an acoustic wave at a depth m within the cardiac tissue. The matrix entries from a single row, for example, the matrix elements $A_{11}, A_{21}, \ldots, A_{N1}$, corresponding to a single depth across all points in time included in the matrix A, are then compared by calculating the absolute differences $d_{11}=|A_{11}-A_{21}|, d_{21}=|A_{21}-A_{31}|, \ldots, d_{(N-1)1}=|A_{(N-1)1}-A_{N1}|$ as a measure of similarity of the sensed contraction signal at neighboring points in time. A small absolute difference thereby indicates that the sensed contraction signal is very similar at the considered neighboring points in time and the considered depth, whereas a large absolute difference indicates that the sensed contraction signal is rather non-similar at the considered neighboring points in time and the considered depth. A threshold $d_{thresh}$ equal to, for example, two-thirds of the maximum absolute difference is then taken and the non-similarity points in time $T_{kl}$, with $1 \leq k \leq (N-1)$, at which the calculated similarity values $d_{11}, d_{21}, \ldots, d_{(N-1)1}$ are greater than the threshold $d_{thresh}$ are found. This is repeated for all values of m, that is, for all different depths in the cardiac tissue, yielding non-similarity points in time $T_{kl}$, with $1 \leq l \leq M$, at which the threshold $d_{thresh}$ is exceeded at a depth l within the cardiac tissue. A one-dimensional histogram $H_k$ of the non-similarity points in time $T_{kl}$ is then taken, wherein the depth l of the non-similarity points in time $T_{kl}$ is neglected. The peaks in the histogram $H_k$ are then taken as the points in time which are used for determining the periodicity and/or phase of the reoccurring local contraction of the heart.

This is shown in FIG. 5B, in which the points in time, at which a reoccurring local contraction of the heart 2 at the sensing site 22 of the heart 2 has been determined, are marked by white vertical lines. These points in time are also shown in FIG. 5C in a corresponding 'binary mode' plot image, wherein it must be noted that the amplitude, in this embodiment, does not correlate with the amplitude of the reoccurring local contraction.

From the 'binary mode' plot image shown in FIG. 5C, a cycle length, periodicity and/or phase of the reoccurring local contraction of the heart 2 at the sensing site 22 of the heart 2 (and the changes therein) can easily be derived.

The apparatus 1 for determining a property of a heart 2, in this embodiment, further comprises a reference signal providing unit 12, shown in FIG. 1, for providing a reoccurring reference signal. In this embodiment, the reference signal providing unit 12 is an electrocardiograph for measuring an ECG (electrocardiogram) signal representing the heart rate and rhythm of the heart 2 as the reoccurring reference signal. The periodicity and/or phase of the reoccurring local contraction of the heart 2 at the sensing site 22 of the heart 2 is determined with respect to the reoccurring reference signal. This allows determining the relationship between the cardiac cycle and the reoccurring local contraction at different sensing sites 22 of the heart 2. The knowledge about the relationship between the cardiac cycle and the reoccurring local contraction at the different sensing sites 22 then makes it possible to determine the sequence in which different parts of the heart 2 are activated.

While the periodicity and/or phase of the reoccurring local contraction at the sensing site 22 of the heart 2 is determined with the above-described method irrespective of the depth, these values can also be determined separately for different depths or depth ranges within the cardiac tissue. This is achieved, for example, by taking for each considered depth or depth range a separate one-dimensional histogram $H_k$ of those non-similarity points in time $T_{kl}$ that lie within the considered depth or depth range within the cardiac tissue, wherein the depth l of these non-similarity points in time $T_{kl}$ is again neglected. The peaks in the histogram $H_k$ are then taken as the points in time which are used for determining the periodicity and/or phase of the reoccurring local contraction of the heart.

Alternatively or in addition to the determination of the periodicity and/or phase, a duration and/or an amplitude, that is, a force, of the reoccurring local contraction of the heart 2 at the sensing site 22 of the heart 2 (and the changes therein) can also be determined. This can be done, for example, by applying an edge detection algorithm to the two-dimensional 'M-mode' image shown in FIG. 5A in order to extract the depth of a recognizable part of the cardiac tissue, such as the front wall 28 or the back wall 29, at the different points in time. The amplitude of the reoccurring local contraction can then be calculated as the difference between the smallest and the largest depth of the extracted recognizable part of the cardiac tissue at the different points in time. Likewise, the duration of the reoccurring local contraction of the heart 2 at the sensing site 22 of the heart 2 can be determined from as, for example, the minimum temporal distance between smallest depths of the extracted recognizable part of the cardiac tissue temporarily enclosing a maximum depth of the extracted recognizable part of the cardiac tissue. At least one of the duration and the amplitude of the reoccurring local contraction of the heart 2 at the sensing site 22 can be determined for different depths within the cardiac tissue by extracting recognizable parts of the cardiac tissue.

While the determination of a reoccurring local contraction of a heart 2 at a sensing site 22 of the heart 2 has been described for the sake of clarity with reference to the two-dimensional 'M-mode' images shown in FIGS. 5A and 5B and the corresponding 'binary plot' image shown in FIG. 5C, it should be clear that these images do not necessarily have to be generated in order to determine certain parameters, for example, the periodicity and/or phase, of the reoccurring local contraction. Moreover, instead of calculating and evaluating differences between neighboring 'A-lines' as similarity values of a similarity measure at neighboring points in time, other ways of determining the reoccurring local contraction may be employed additionally or in an alternative. For example, as another similarity measure for generating similarity values of the sensed contraction signal at neighboring points in time, a correlation between neighboring 'A-lines' can be calculated and compared to a threshold. A correlation value below the threshold signifies a non-similarity point in time, that is, a point in time at which the heart 2 exhibited a reoccurring local contraction at the sensing site 22 of the heart 2.

Figure 6:
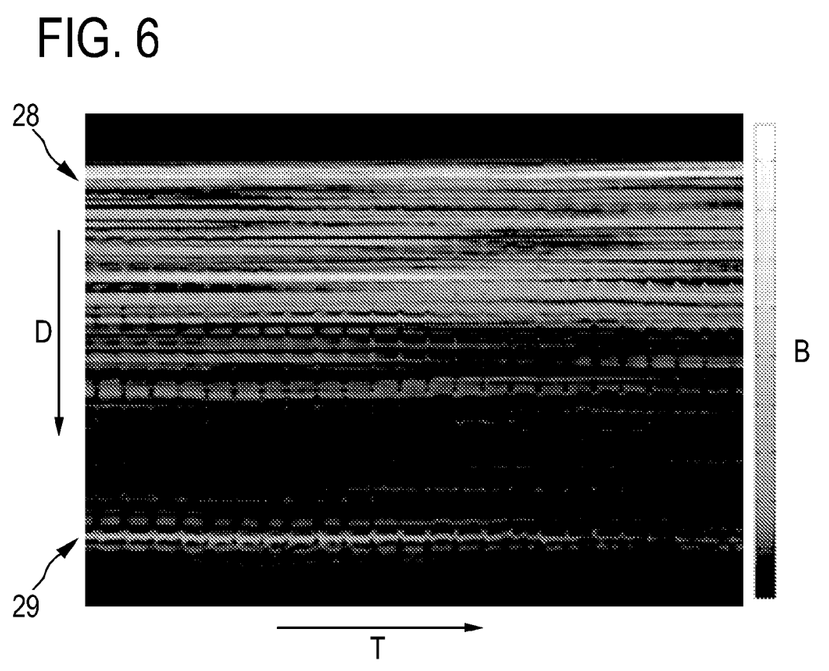
FIG. 6 shows schematically and exemplarily the temporal behavior of a contraction signal indicative of a reoccurring local contraction of a heart sensed at a sensing site of the heart by a first property sensing unit.

FIG. 6 shows schematically and exemplarily the temporal behavior of a contraction signal indicative of a reoccurring local contraction of a heart 2 sensed at a sensing site 22 of the heart 2 by a first property sensing unit 21.

In this embodiment, the contraction signal is visualized as a two-dimensional 'M-mode' image as described with reference to FIG. 4. Since the heart 2 exhibits a reoccurring local contraction at the sensing site 22, a corresponding reoccurring local displacement of the cardiac tissue can be recognized in the two-dimensional 'M-mode' image. In contrast to the two-dimensional 'M-mode' image shown in FIG. 5A, however, the contraction signal has been sensed with the distal end 6 of the catheter 5 being in direct contact with the heart 2. This is the configuration that would typically apply during an ablation procedure with a catheter 5 as shown in FIG. 2A or 2B. The reoccurring local contraction of the heart 2 at the sensing site 22 of the heart 2 can be determined from the sensed contraction signal according to the above-described method.

Figure 7A:
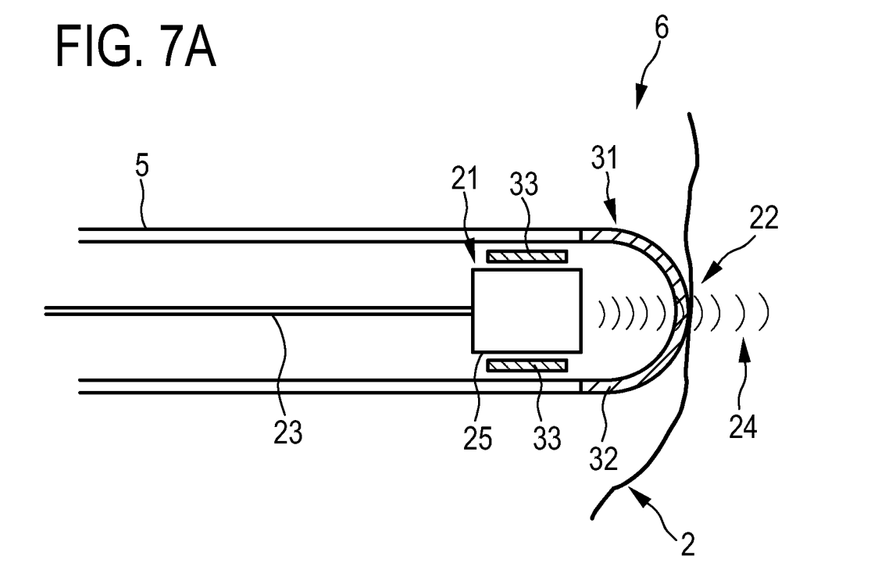
FIGS. 7A, 7B show schematically and exemplarily two embodiments of a distal end of a catheter for use in an apparatus for determining a property of a heart.

FIG. 7A shows schematically and exemplarily an embodiment of a distal end 6 of a catheter 5 for use in an apparatus 1 for determining a property of a heart 2.

In the embodiment shown in FIG. 7A, the catheter 5 comprises a first property sensing unit 21, which in this embodiment is an acoustic sensing unit comprising a single element ultrasound transducer 25, for sensing a contraction signal indicative of a reoccurring local contraction of a heart 2 at a sensing site 22 of the heart 2. The first property sensing unit 21 is connectable to the first property determining unit 8, shown in FIG. 1, via a connection 23 suitable for conveying the contraction signal from the first property sensing unit 21 to the first property determining unit 8. The connection 23 can be, for example, an electrical connection or an optical connection.

The catheter 5, in this embodiment, comprises a further property sensing unit 31 for sensing a property signal indicative of a further property of the heart 2 at the sensing site 22 of the heart 2. The further property sensing unit 31, in this embodiment, comprises at least one electrode 32 for sensing an electrical property, such as the conduction and/or impedance of the heart 2 at the sensing site 22 of the heart 2. The electrode 32 is an acoustically transparent electrode, for example, a TPX electrode with a thin metallic coating on the frontside or an electrode made of another acoustically transparent material such as doped polymer. Additionally or alternatively, the further property sensing unit 31 can also comprise a temperature sensor for sensing a temperature or any other sensor for sensing a suitable further property of the heart 2 at the sensing site 22 of the heart 2. The further property sensing unit 31 is connectable to a further property determining unit 13 comprised by the catheter control unit 7 shown in FIG. 1 of the apparatus 1 for determining a property of a heart 2 via a connection (not shown in FIG. 7A) suitable for conveying the property signal from the further property sensing unit 31 to the further property determining unit 13. The connection can be, for example, an electrical connection or an optical connection.

The apparatus 1 for determining a property of a heart 2, in particular, in this embodiment, the catheter 5, further comprises a position determining unit 33 for determining a position of the sensing site 22. For example, the position of the sensing site 22 can be determined by determining the position of the distal end 6 of the catheter 5 using electrical or magnetic localization or GPS and by deriving the position of the sensing site 22 from the determined position of the distal 6 of the catheter 5. In an embodiment, the position determining unit 33 can be a system such as LocaLisa™ or Real-Time Position Management™. Alternatively, the position of the distal end 6 of the catheter 5 and, thus, the position of the sensing site 22, can be extracted from real-time image data such as fluoroscopy, magnetic resonance imaging, ultrasound imaging or computed tomography imaging. The real-time image data can be provided, for example, by the fluoroscopy device shown in FIG. 1.

The first property sensing unit 21 and the first property determining unit 8, in this embodiment, are adapted to determine the reoccurring local contraction of the heart 2 at different sensing sites 22 of the heart 2 and the position determining unit 33 is adapted to determine the positions of the different sensing sites 22. For example, the distal end 6 of the catheter 5 can be guided to different sensing site 22 of the heart 2 in order to determine the reoccurring local contraction of the heart 2 at the different sensing sites 22 of the heart 2 and to determine the positions of the different sensing sites 22.

Moreover, the apparatus 1 for determining a property of a heart 2, in particular, the catheter control unit 7, comprises a map generation unit 14, shown in FIG. 1, for generating a contraction map of the heart 2 based on the determined reoccurring local contraction at the different sensing sites 22 and the determined positions of the different sensing sites 22. The contraction map represents the reoccurring local contraction of the heart 2 at the positions of the different sensing sites 22.

In this embodiment, the further property sensing unit 31 and the further property determining unit 13 are adapted to additionally determine the further property of the heart 2 at the different sensing sites 22 of the heart 2 and the map generation unit 14 is adapted to generate a contraction map of the heart 2 which additionally represents the further property of the heart 2 at the positions of the different sensing sites 22 based on the determined further property at the different sensing sites 22 and the determined positions of the different sensing sites 22.

Figure 7B:
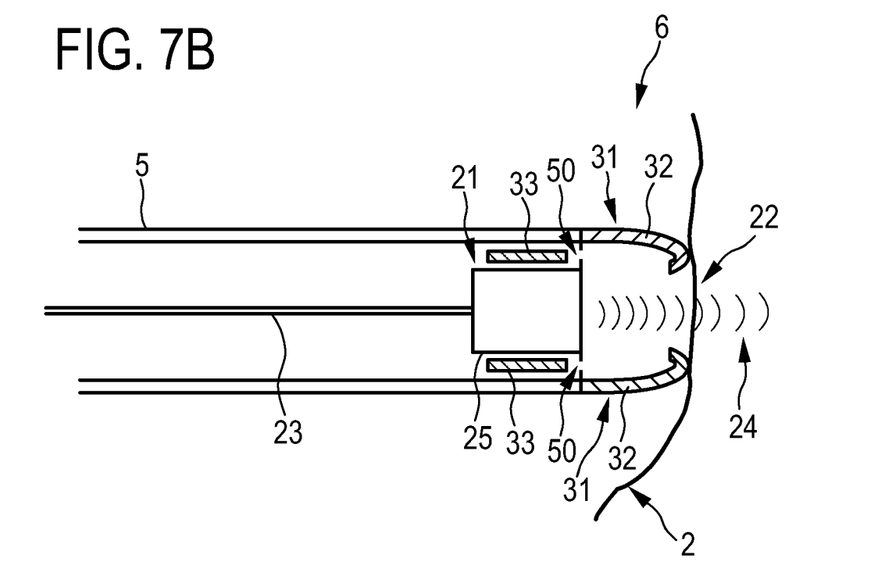

FIG. 7B shows schematically and exemplarily a further embodiment of a distal end 6 of a catheter 5 for use in an apparatus 1 for determining a property of a heart 2.

In the embodiment shown in FIG. 7B, the catheter 5 differs from the one shown in FIG. 7A in that the electrode 32 comprised by the further property sensing unit 31 is an annular electrode. The annular electrode 32 and the first property sensing unit 21 together form a kind of channel through which the acoustic waves 24 are transmitted. In order to avoid the presence of air and/or blood in front of the first property sensing unit 21, the channel is preferentially filled with an irrigation fluid (not shown in FIG. 7B), for example, a saline solution, that is pumped through the lumen of the catheter 5 and that can leave the lumen through openings 50. The lumen can be completely filled by the irrigation fluid or a tube can be present within the lumen of the catheter 5, wherein the tube is connected to the openings 50 such that the irrigation fluid can leave the catheter 5 through the openings 50.

Figure 8:
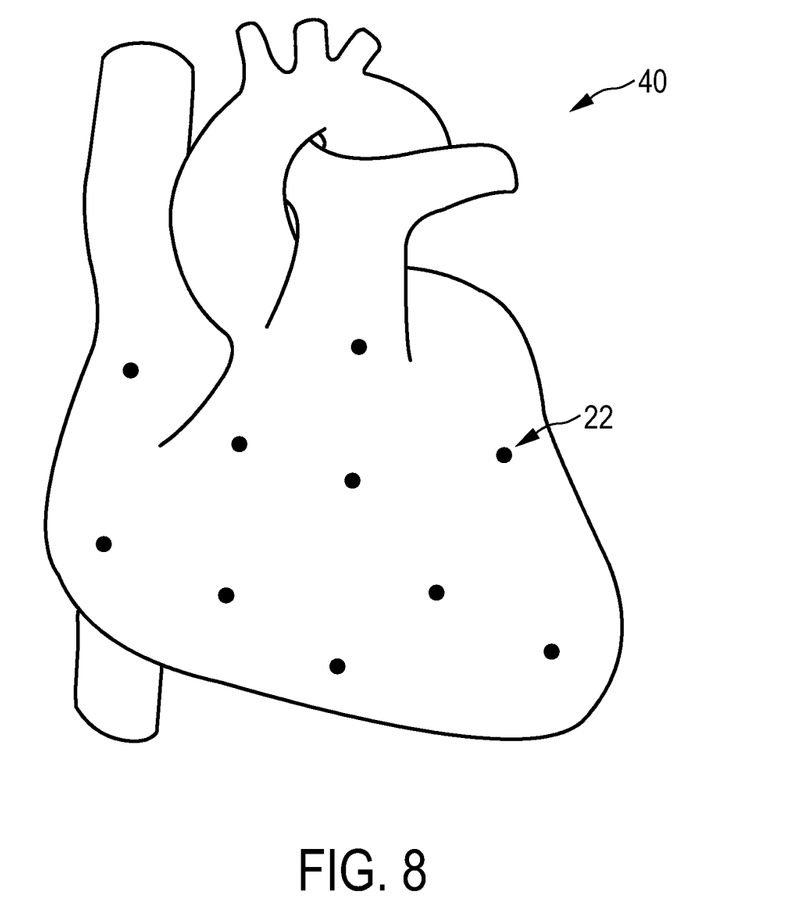
FIG. 8 shows schematically and exemplarily an embodiment of a contraction map of a heart.

FIG. 8 shows schematically and exemplarily an embodiment of a contraction map 40 of a heart 2. The contraction map 40 exhibits a plurality of sensing sites 22, in FIG. 8 indicated by bullets 22, at different positions of the heart 2. The contraction map 40 represents the reoccurring local contraction of the heart 2 at the different positions of the sensing sites 22 of the heart 2. This information can be presented to a user such as a clinician in any suitable manner, for example, by intensity- and/or color-coding the periodicity and/or phase and/or amplitude of the reoccurring local contraction of the heart 2 at the different positions of the sensing sites 22 of the heart 2. The contraction map 40 can be visualized, for example, on a display.

Preferentially, the contraction map 40 additionally represents a further property of the heart 2 at the different positions of the sensing sites 22 of the heart 2. The further property can be, for example, an electrical property, such as the conduction and/or impedance of the heart 2 at the sensing sites 22 of the heart 2, or it can be a temperature or any other suitable further property of the heart 2 at the sensing site 22 of the heart 2. The further property can be represented in the contraction map 40, for example, by using different intensities and/or colors and/or shaped markers et cetera.

Figures 9, 10, 11:
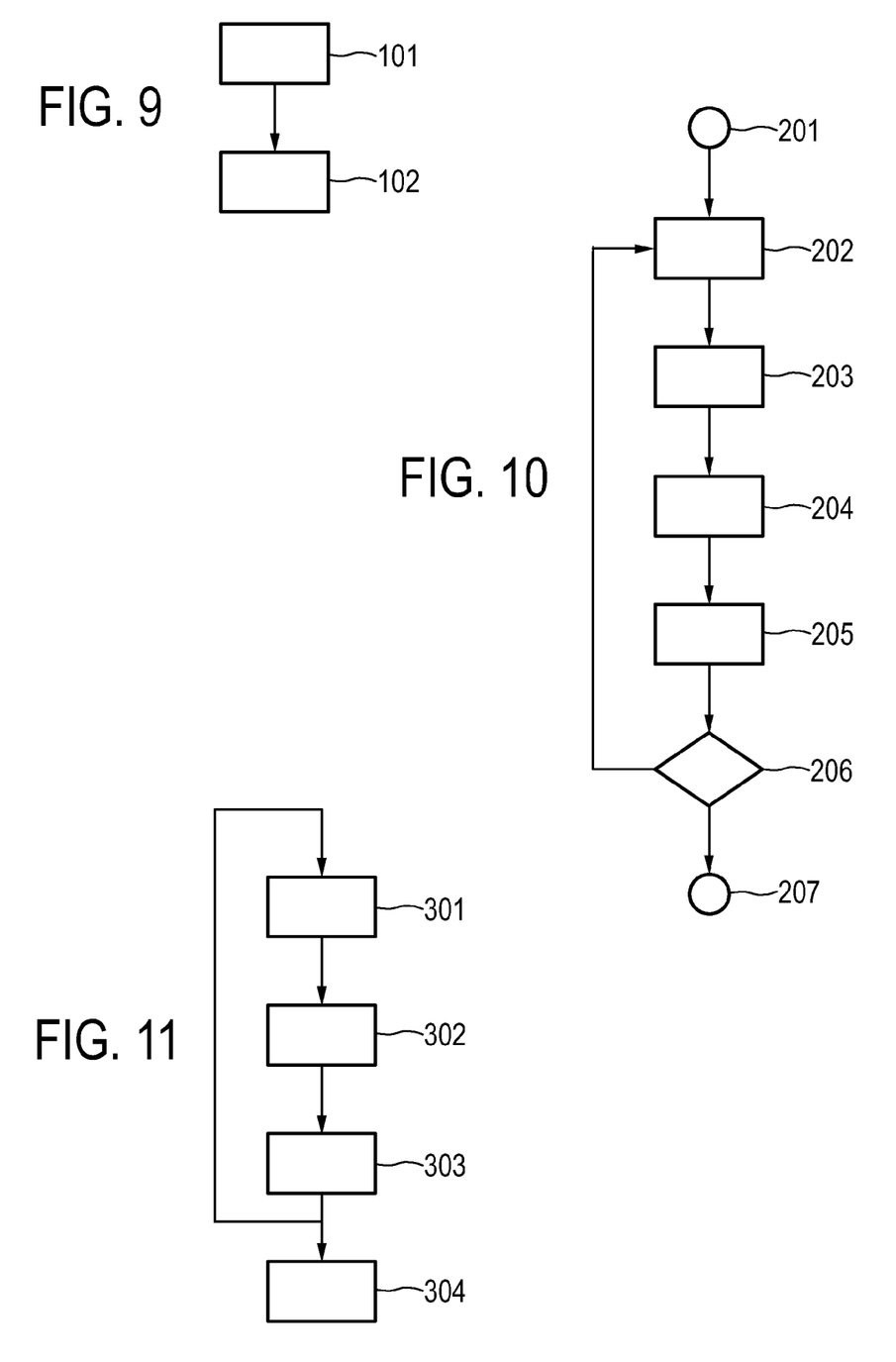
FIG. 9 shows a flowchart exemplarily illustrating an embodiment of a method for determining a property of a heart.
FIG. 10 shows a flowchart exemplarily illustrating an embodiment of a method for determining a progress of ablation during an ablation applied to a heart.
FIG. 11 shows a flowchart exemplarily illustrating an embodiment of a method for generating a contraction map of a heart.

FIG. 9 shows a flowchart exemplarily illustrating an embodiment of a method for determining a property of a heart 2.

In step 101, a contraction signal indicative of a reoccurring local contraction of the heart 2 at a sensing site 22 of the heart 2 is sensed by means of a first property sensing unit 21 comprised in a catheter 5.

In step 102, the reoccurring local contraction of the heart 2 at the sensing site 22 of the heart 2 is determined from the sensed contraction signal as a first property of the heart 2 by means of a first property determining unit 8.

FIG. 10 shows a flowchart exemplarily illustrating an embodiment of a method for determining a progress of ablation during an ablation applied to a heart 2.

Before ablation starts in an initialization step 201, a contraction signal indicative of a reoccurring local contraction of the heart 2 at a sensing site 22 of the heart 2 is sensed by means of a first property sensing unit 21 comprised in a catheter 5 and a reoccurring local contraction of the heart 2 at the sensing site 22 of the heart 2 is determined from the sensed contraction signal as a first property of the heart 2 by means of a first property determining unit 8. The initially determined reoccurring local contraction of the heart provides a reference value that represents the reoccurring local contraction of the heart 2 at the sensing site 22 of the heart 2 before the start of ablation.

In step 202, energy is applied to the heart 2 at the sensing site 22 of the heart 2 by means of an energy applying unit 26 comprised in a catheter 5 for ablating cardiac tissue at the sensing site.

In step 203, a contraction signal indicative of a reoccurring local contraction of the heart 2 during or after ablation at a sensing site 22 of the heart 2 is sensed by means of the first property sensing unit 21 comprised in the catheter 5.

In step 204, the reoccurring local contraction of the heart 2 during or after ablation at the sensing site 22 of the heart 2 is determined from the sensed contraction signal as a first property of the heart 2 by means of the first property determining unit 8.

Steps 203 and 204 are executed after the start of ablation and provide a current value that represents the reoccurring local contraction of the heart 2 at the sensing site 22 of the heart 2 at the current state of ablation. The reference value and the respective current value can be, for example, the periodicity and/or phase and/or amplitude and/or duration of the reoccurring local contraction of the heart 2 at the sensing site 22 of the heart 2.

In step 205, the progress of ablation is determined based on the determined reoccurring local contraction by comparing the respective current value and the reference value, for example, by calculating a difference. For example, before the start of ablation a reference value can be determined being, for instance, a reference periodicity and/or a reference phase and/or a reference amplitude and/or a reference duration of contraction et cetera. This reference value is compared with the respective current value, which is determined during ablation or after ablation has been performed, in order to determine a change in the reoccurring local contraction of the heart at the sensing site, for example, for determining an increasing period of the reoccurring local contraction or an decreasing amplitude of the reoccurring local contraction. This change is preferentially used for monitoring the ablation progress.

In step 206 it is determined whether a desired degree of ablation progress has been reached. If this is the case, at the current sensing site the ablation is stopped in step 207 and the whole ablation procedure can be terminated or the catheter 5 can be guided to another sensing site, wherein at these new sensing site steps 201 to 206 can be repeated. If it is determined that the degree of ablation is not sufficient, the method continues with step 202. For determining whether the degree of ablation is sufficient, the change determined in step 205 can be compared with a threshold, wherein, if the determined change exceeds the threshold, it is decided that the degree of ablation is sufficient.

Steps 202 to 206 can be performed in another logical sequence. Furthermore, some steps can be performed simultaneously, for example, step 202 and 203, 204.

FIG. 11 shows a flowchart exemplarily illustrating an embodiment of a method for generating a contraction map 40 of a heart 2.

In step 301, a contraction signal indicative of a reoccurring local contraction of the heart 2 at a sensing site 22 of the heart 2 is sensed by means of a first property sensing unit 21 comprised in a catheter 5

In step 302, the reoccurring local contraction of the heart 2 at the sensing site 22 of the heart 2 is determined from the sensed contraction signal as a first property of the heart 2 by means of a first property determining unit 8.

In step 303, the position of the sensing site 22 is determined by means of a position determining unit 33.

Steps 301 to 303 are repeated for a desired number of different sensing sites 22 of the heart 2. Thereafter, the method continues to step 304.

Steps 301 and 302 and step 303 can be performed simultaneously or in any other order. For example, step 303 can be performed before performing steps 301 and 302.

In step 304, a contraction map 40 of the heart 2 is generated based on the determined reoccurring local contraction at the different sensing sites 22 and the determined positions of the different sensing sites 22 by means of a map generation unit 14, wherein the contraction map 40 represents the reoccurring local contraction at the positions of the different sensing sites 22.

In steps 301 and 302, a further property of the heart 2 at the sensing site 22 can be determined by using the further property sensing unit 31 and the further property determination unit 13. For example, the conduction and/or impedance and/or temperature of the heart 2 at the sensing site 22 of the heart 2 can be determined. In step 304, also these determined further properties can be represented in the contraction map 40, for example, by using different intensities and/or color and/or shaped markers et cetera.

Although the catheter comprising an energy applying unit and the catheter comprising a further property sensing unit have been described as different embodiments, the present invention can also be used in a combined catheter, that is, in a catheter that comprises both an energy applying unit and a further property sensing unit. In some embodiments, the same unit may be used both for applying energy to the heart and for determining a further property of the heart at a sensing site of the heart.

Although in the above described embodiments certain arrangements of elements of a catheter tip have been schematically and exemplarily described and shown in FIGS. 2A, 2B, 7A, 7B, the invention is not limited to these constructions of the catheter tip. For example, if the annular electrode 27 is used, the catheter tip can also be manufactured without an irrigation means. Moreover, also the catheter tip shown in FIGS. 2A and 7A can comprise an irrigation means. It is also possible that the catheter tip comprises the first property sensing unit, which is preferentially an ultrasound transducer, without comprising an electrode. Any apparatus for determining a property of a heart which comprises a catheter comprising a first property sensing unit for sensing a contraction signal indicative of a reoccurring local contraction of the heart at a sensing site of the heart and a first property determining unit for determining the reoccurring local contraction of the heart at the sensing site from the sensed contraction signal as a first property of the heart is within the scope of the invention.

The contraction map can represent the reoccurring local contraction and the further property at the same positions or at different positions, for example, the further properties can be determined at positions being different to the positions of the sensing sites at which the reoccurring local contraction is determined, wherein the contraction map shows the further property and the reoccurring local contraction at the respective positions. Furthermore, even if a further property and a reoccurring local contraction are sensed at the same sensing site, the contraction map can show the reoccurring local contraction and the further property side-by-side at the position of the sensing site.

While the invention has been illustrated and described in detail in the drawings and foregoing description, such illustration and description are to be considered illustrative or exemplary and not restrictive; the invention is not limited to the disclosed embodiments. Other variations of the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single device or other unit may fulfill the functions of several items recited in the claims. There mere fact that certain measures are recited in mutually different dependent claims does not indicate that a combination of these measures cannot be used to advantage.

Several functions which are realized by different units in the above-described embodiments can be realized by any number of units, also by a single unit.

A computer program may be stored/distributed on a suitable medium, such as an optical storage medium or a solid-state medium supplied together with or as part of other hardware, but may also be distributed in other forms, such as via the internet or other wired or wireless telecommunication systems.

Any reference signs in the claims should not be construed as limiting the scope of the invention.

The invention claimed is:

1. An apparatus for determining a property of a heart (2), wherein the apparatus (1) comprises:
    a catheter (5) comprising a first property sensing unit (21) structurally configured to emit and receive imaging energy for sensing a contraction signal indicative of a reoccurring local contraction of the heart (2) at a sensing site (22) of the heart (2), and
    a first property determining unit (8) for determining at least one of a periodicity and a phase of the reoccurring local contraction of the heart (2) at the sensing site (22) from the sensed contraction signal as a first property of the heart (2).

2. The apparatus according to claim 1,
    wherein the apparatus (1) comprises a reference signal providing unit (12) for providing a reoccurring reference signal and
    wherein the first property determining unit (8) is adapted to determine at least one of the periodicity and the phase of the reoccurring local contraction with respect to the reoccurring reference signal.

3. The apparatus according to claim 1,
    wherein the first property sensing unit (21) is adapted to sense the contraction signal at different points in time,
    wherein the first property determining unit (8) is adapted to:
        apply a similarity measure for comparing the sensed contraction signal at neighboring points in time resulting in similarity values indicating the similarity of the sensed contraction signal at the neighboring points in time,
        determine non-similarity points in time by comparing the similarity values to a threshold,
        determine at least one of the periodicity and the phase of the reoccurring local contraction of the heart (2) from the determined non-similarity points in time.

4. The apparatus according to claim 1, wherein the first property determining unit (8) is adapted to determine an amplitude of the reoccurring local contraction.

5. The apparatus according to claim 1, wherein the first property sensing unit (21) is an acoustic sensing unit for emitting acoustic waves (24) for being reflected at one or more depths within the heart (2) and for receiving the reflected acoustic waves (24), wherein the sensed contraction signal depends on the received acoustic waves (24).

6. The apparatus according to claim 1,
    wherein the catheter (5) comprises a further property sensing unit (31) for sensing a property signal indicative of a further property of the heart (2) at the sensing site (22) and
    wherein the apparatus (1) comprises a further property determining unit (13) for determining the further property of the heart (2) at the sensing site (22) from the sensed property signal.

7. The apparatus according to claim 1, wherein the catheter (5) comprises an energy applying unit (26) for applying energy to the heart (2).

8. The apparatus according to claim 7,
    wherein the energy applying unit (26) is adapted to ablate the heart (2) and
    wherein the apparatus (1) comprises an ablation progress determining unit (11) for determining a progress of ablation based on the determined reoccurring local contraction.

9. The apparatus according to claim 1, wherein the apparatus (1) comprises a position determining unit (33) for determining a position of the sensing site (22).

10. The apparatus according to claim 9,
    wherein the first property sensing unit (21) and the first property determining unit (8) are adapted to determine the reoccurring local contraction at different sensing sites (22) of the heart (2),
    wherein the position determining unit (33) is adapted to determine the positions of the different sensing sites (22), and
    wherein the apparatus further comprises a map generation unit (14) for generating a contraction map (40) of the heart (2) based on the determined reoccurring local contraction at the different sensing sites (22) and the determined positions of the different sensing sites (22), wherein the contraction map (40) represents the reoccurring local contraction at the positions of the different sensing sites (22).

11. The apparatus according to claim 10,
    wherein the catheter (5) comprises a further property sensing unit (31) for sensing a property signal indicative of a further property of the heart (2) at the sensing site (22) and
    wherein the apparatus (1) comprises a further property determining unit (13) for determining the further property of the heart (2) at the sensing site (22) from the sensed property signal,
    wherein the further property sensing unit (31) and the further property determining unit (13) are adapted to additionally determine the further property at the different sensing sites (22) of the heart (2), and
    wherein the map generation unit (14) is adapted to generate a contraction map (40) of the heart (2) which additionally represents the further property at the positions of the different sensing sites (22) based on the determined further property at the different sensing sites (22) and the determined positions of the different sensing sites (22).

12. A method for determining a property of a heart (2), wherein the method comprises the following steps:
    emitting and receiving imaging energy by a first property sensing unit (21) comprises in a catheter (4);

sensing a contraction signal indicative of a reoccurring local contraction of the heart (2) at a sensing site (22) of the heart (2), by a first property sensing unit (21) comprised in a catheter (4); and determining at least one of a periodicity and a phase of the reoccurring local contraction of the heart (2) at the sensing site (22) from the sensed contraction signal as a first property of the heart (2) by a first property determining unit (8).

13. A non-transitory computer program for determining a property of a heart (2), wherein the computer program comprises program code for causing a computer to carry out the following steps when the computer program is run on the computer:

emitting and receiving imaging energy by a first property sensing unit (21) comprises in a catheter (4);

sensing a contraction signal indicative of a reoccurring local contraction of the heart (2) at a sensing site (22) of the heart (2), by a first property sensing unit (21) comprised in a catheter (4); and determining at least one of a periodicity and a phase of the reoccurring local contraction of the heart (2) at the sensing site (22) from the sensed contraction signal as a first property of the heart (2) by a first property determining unit (8).

* * * * *